United States Patent [19]

Lim et al.

[11]  4,251,387
[45]  Feb. 17, 1981

[54] PROCESS FOR PREPARING SEMIPERMEABLE MICROCAPSULES

[75] Inventors: Franklin Lim, Richmond; Richard D. Moss, Chester, both of Va.

[73] Assignee: Damon Corporation, Needham Heights, Mass.

[21] Appl. No.: 30,847

[22] Filed: Apr. 17, 1979

Related U.S. Application Data

[63] Continuation-in-part of Ser. No. 606,166, Aug. 20, 1975, which is a continuation-in-part of Ser. No. 931,177, Aug. 4, 1978, abandoned.

[51] Int. Cl.$^3$ .............................................. B01J 13/02
[52] U.S. Cl. .................................. 252/316; 210/656; 264/4; 424/32; 424/85; 424/94; 424/125; 424/177; 424/DIG. 7
[58] Field of Search ........................... 252/316; 424/32

[56] References Cited

U.S. PATENT DOCUMENTS

| | | | |
|---|---|---|---|
| 3,429,827 | 2/1969 | Ruus | 252/316 |
| 3,577,515 | 5/1971 | Vandegaer | 252/316 X |
| 3,864,275 | 2/1975 | Kan et al. | 252/316 |

FOREIGN PATENT DOCUMENTS

| | | | |
|---|---|---|---|
| 873815 | 6/1971 | Canada | 252/316 |
| 1600988 | 9/1970 | France | 252/316 |

*Primary Examiner*—Richard D. Lovering
*Attorney, Agent, or Firm*—Kenway & Jenney

[57] ABSTRACT

Techniques for producing semipermeable microcapsules by interfacial polymerization are disclosed. The material to be encapsulated and a hydrophilic monomer are emulsified within a hydrophobic continuous phase. Polymerization is initiated by dissolving a second monomer in the continuous phase, and occurs only at the interface of the emulsion to result in the formation of macroporous, poorly defined capsule membranes. Next, the affinity of the continuous phase for the hydrophilic monomer is varied by altering the polarity of the continuous phase. This step is accomplished either by isolating and resuspending the raw capsules in a fresh continuous phase of different polar character, or by mixing a second solvent with the continuous phase. By controlling the affinity and the concentration of the second monomer, it is possible to produce microcapsules having uniform capsule membranes and a selected upper limit of permeability.

12 Claims, No Drawings

PROCESS FOR PREPARING SEMIPERMEABLE MICROCAPSULES

CROSS REFERENCE TO RELATED APPLICATIONS

This application is a continuation in part of copending U.S. application Ser. No. 606,166, filed Aug. 20, 1975, entitled "Encapsulation of Labile Biological Materials", and Ser. No. 931,177, filed Aug. 4, 1978, and now abandoned, entitled "Controlled Porosity Microcapsules", both to F. Lim et al, the teachings of which are incorporated herein by reference.

BACKGROUND OF THE INVENTION

This invention relates to an encapsulation process and more particularly to a process for producing semipermeable microcapsules.

U.S. application Ser. Nos. 606,166 and 931,177, now abandoned, disclose novel techniques for encapsulating chemically active materials in microcapsules whose uniformity of structure and permeability are controlled to an improved degree such that relatively low molecular weight substances with which the encapsulated substance can react can diffuse through the capsule membranes, yet passage of the encapsulated substance is prevented. The techniques of these applications, in addition to providing an improved degree of control over the permeability of the capsule membranes, also enable encapsulation of easily denaturedmaterials such as enzymes and various antibodies such that they remain biochemically operative. These microencapsulation procedures constitute improvements over the well-known interfacial polymerization technique which utilizes the interface of an emulsion as a reaction zone wherein a first monomer solubilized in the discontinuous phase forms a polymeric membrane with a second, complementary monomer dissolved in the continuous phase.

SUMMARY OF THE INVENTION

It has now been discovered that the microencapsulation techniques disclosed in the above-referenced applications, suitably modified, may be used to encapsulate essentially any core material within membranes having an upper limit of permeability wihin a selected range. The permeability of the microcapsules is determined during membrane formation by controlling certain parameters of the interfacial polymerization reaction. Briefly, a first, hydrophilic monomer capable of forming a copolymer by polycondensation or polyaddition reaction with a second, hydrophobic, complementary monomer is dissolved in water together with the material (if ay) to be encapsulated, and the solution is emulsified within a hydrophobic solvent. When a portion of the complementary monomer is dissolved in the continuous phase of the emulsion, membrane formation begins as interfacial polymerization takes place about the droplets of the discontinuous phase.

In accordance with the invention, the polymerization reaction is allowed to continue only until macroporous, poorly formed capsule membranes are produced, and in a second stage, the affinity of the continuous phase for the first monomer contained in the discontinuous phase droplets is varied by altering the polarity of the continuous phase so that further polymerization occurs preferentially within the macroporous capsule membranes, or in a second, outer layer. Finally, the polymerization is terminated when microcapsules of the selected upper limit of permeability have been produced. The technique of varying the affinity of the continuous phase for the monomers dissolved in the discontinuous phase droplets enables one to exercise a degree of control over the thickness of the interface and thus over the site of polymer formation. Further, it allows one to minimize side reactions between continuous phase-solubilized monomers, e.g., diacid chlorides, and water in the discontinuous phase.

In one embodiment, the continuous phase at the outset has a relatively high affinity for the encapsulated monomer so that a relatively thick polymer network is produced about the droplets where the monomers meet. In a second stage of polymerization, the continuous phase is altered to have a low affinity for the first monomer, resulting in the precipitation of polymer preferentially within the voids of the raw capsules. In a preferred embodiment, the continuous phase in the first stage has a low affinity for the encapsulated monomer so that a thin polymer membrane is produced at the interface, and in the second stage, the continuous phase is altered to have a relatively high affinity for the first monomer. Thus, additional quantities of first monomer are drawn through the initially formed membranes and made available for reaction with further quantities of second monomer. In both embodiments, the upper limit of permeability can be varied with improved precision by controlling the duration of the first and second stage reactions, the polarity of the continuous phase, the concentrations of the monomers, and by including small amounts, e.g., 0–5%, of a multifunctional cross-linking substances with one of the monomers.

The complementary monomer which is soluble in the continuous phase is preferably added in increments over the course of the reaction. This results in a lessening of the side reactions between water from the droplet phase and the hydrophobic monomer, which terminates polymer chain formation.

Two techniques for varying the affinity of the continuous phase for encapsulated monomers have been employed with success. As disclosed in U.S. Application Ser. No. 606,166, the partly formed first stage microcapsules can be separated from the two-phase system and resuspended in a fresh continuous phase of a solvent or solvent system having a polarity different from the originally employed continuous phase. Alternatively, a continuous phase-miscible solvent can be use to dilute the original continuous phase to vary its net polarity. If the material sought to be encapsulated is easily denatured, e.g., an antibody or an enzyme, the pH of the discontinuous phase is controlled so that the labile material retains much of its biological activity. Thus, a buffered solution having a pH suitable for maintenance of the antibody, etc., often including a stabilizing carrier such as polyvinyl pyrrolidone, albumin, or dextran, may be used as the discontinuous droplet phase.

In a preferred process, polyamide microcapsules are produced from a hydrophilic monomer comprising a multifunctional amine and a hydrophobic monomer comprising a difunctional acid halide. The amine can comprise a difunctional monomer mixed with from 0–50% of a polyfunctional cross-linker, e.g., tetraethylenepentamine, although successful microencapsulations have been done using only pentamines. In general, the higher the concentration of polyfunctional amine used in the aqueous discontinuous phase, the lower the permeability limit. Preferred amines include 1, 6 hexane diamine, 2, 5-dimethylpiperazine, 1, 4 butane diamine, and propylene diamine. Preferred difunctional acid halides include terephthaloyl chloride and sebacyl chloride. For the foregoing polymer systems, the preferred continuous phase solvents comprise cyclohexane, diluted or mixed with chloroform as appropriate. The affinity of pure cyclohexane for the amines is low; dilution with chloroform results in a mixed solvent of increased affinity for amine.

When a hydrophilic material of molecular weight in excess of the permeability limit of the membranes is enclosed within capsules of a permeability sufficient to allow passage of certain relatively low molecular weight materials (e.g., below about 5,000 daltons), the microcapsules may be used in a column or the like as a "molecular sieve" to separate a mixture of substances of differing molecular weights of a magnitude within the molecular weight range of materials which can traverse the capsule membranes. If an antibody or other specific binding substance is encapsulated in membranes having an upper limit of permeability too low to allow its diffusion, the microcapsules may be used in an immunospecific column suitable for selectively extracting the complementary substance of the antibody from a mixture of materials.

Accordingly, it is an object of the invention to provide a process for producing semipermeable microcapsules useful as a chromatographic separation material. Another object is to encapsulate chemically inactive materials and operable biologically and chemically active materials. Still other objects are to provide a method of controlling capsule membrane permeability to an improved degree and a method which may be practiced using a large variety of monomers which react to form polymeric chains by polycondensation or polyaddition.

These and other objects and features of the invention will be apparent from the following description of some preferred embodiments.

DESCRIPTION OF THE PREFERRED EMBODIMENT

The process of the invention involves a novel variation in the well known process for microencapsuation known generally as interfacial polymerization. This technique utilizes a pair of mutually immiscible solvents or solvent systems, one being hydrophobic, and the other being water. The material to be encapsulated and a first hydrophilic monomer are dissolved in water, and the solution is emulsified to form an aqueous, discontinuous or droplet phase. The size of the droplets determines the size of the microcapsules that will be produced. Emulsification can be effected by any of the well-known emulsification techniques such as, for example, using a blender, and is usually done with the aid of an emulsifing agent. Since the size of the discontinuous phase droplets produced in any given technique and thus the size of the resulting capsules will vary within a specific range, one or more filters may be used to separate oversized or undersized capsules made in any given run to minimize differences in capsule diameter. For a detailed disclosure of the method of varying capsule size, reference should be made to Artificial Cells, Thomas M.S. Chang, Chapt. 2.

When droplets of a selected size have been produced, a second hydrophobic monomer, soluble in the continuous phase, and capable of forming a polymer by polycondensation or polyaddition with the first monomer is introduced into the suspension. Polymerization occurs at the interface of the two-phase system where the complementary monomers meet. The monomers must be chosen from among those which exhibit suitable solubility properties in the solvents selected.

Utilizing this prior art technique, one can exert only crude control on capsule membrane quality, uniformity, and permeability. Thus, if polymerization is terminated at an early stage when the membranes are incompletely formed, the resulting microcapsules have widely varying permeability and are typically characterized by a high frequency of macroporous defects where little or no polymerization has occurred. The result is a quantity of microcapsules, many of which are incapable of confining even high molecular weight materials. On the other hand, if the polymerization is allowed to go to completion, dense, substantially impermeable microcapsules are produced.

In accordance with the invention, the permeability and uniformity of the microcapsule membranes are controlled to an improved degree by varying the affinity of the continuous phase for the discontinuous phase monomer during the course of polymerization. Thus, the thickness of the interface and the amount of first monomer which is available for reaction with the complementary monomer in the continuous phase can be controlled to result in membranes having a relatively uniform permeability. Further, within limits, it is possible to tailor the membranes such that they only allow diffusion of molecules below a selected molecular weight, generally within the range of 200 to 30,000 daltons, and are impermeable to higher molecular weight materials.

In one preferred embodiment, the continuous phase in the first polymerization stage is selected to have a low affinity for the first monomer. This results in the formation of a thin membrane in a narrow interface zone where the complementary monomers come into contact. In a second stage, the affinity of the continuous phase for the first monomer is increased so that additional quantities of the monomer permeate the initially formed membrane layer, one or more additional layers of polymers are formed about the first, and imperfections in the first layer are filled in.

In another embodiment, the affinity of the continuous phase for the first monomer is relatively high at the outset, resulting in the formation of a relatively thick, sponge-like polymer framework. In a second stage, the affinity of the continuous phase for the first monomer is decreased so that further polymerization occurs preferentially within the structure of the initially deposited polymer network, filling in the voids and resulting in uniform capsules.

Two methods of varying the affinity of the continuous phase for the first monomer are contemplated. Thus, the raw capsules may be isolated by, for example, aspiration of the continuous phase and washing, and then resuspended in a fresh quantity of a solvent of different polarity. Further polymerization is then initiated by dissolving, in some cases incrementally, additional quanitities of second monomer in the fresh continuous phase to complete the interfacial polymerization. In another method, the affinity of the continuous phase for the first monomer is increased or decreased as desired by diluting the continuous phase with a solvent, miscible with the originally employed solvent, which progressively varies the net polarity of the continuous phase.

From the foregoing it will be appreciated that the improved degree of control over the permeability and quality of microcapsules made in accordance with the invention is achieved by varying the nature of the interface during the course of the interfacial polymerization, and that this is made possible by controlling the polarity of the continuous phase. Anotherimportant feature of the process of the invention is its inherent ability to overcome the effect of side reactions between the second monomer and water present at the interface. Such reactions form monofunctional monomers which can prematurely terminate polymer chains and disrupt membrane formation. The concentration of these materials at the interface is limited in the two-stage procedure of the invention, especially in the embodiment where the original continuous phase is replaced.

In a preferred reaction system, a multifunctional amine and a high molecular weight, hydrophilic filler material such as polyvinyl pyrrolidone, albumin, dextran, or polyethylene glycol is included in the aqueous phase. The filler material serves to prevent collapse of the finally formed microcapsules. The continuous phase, at the outset, consists of a diacid halide dissolved in pure cyclohexane or a solvent system comprising cyclohexane mixed with a small amount of chloroform, both of which have a low affinity for water soluble monomers. The second stage of polymerization is then effected in a continuous phase comprising a cyclohexane based solvent richer in chloroform, which has increased affinity for water soluble monomers. Conversely, at the outset the continuous phase can comprise a chloroform-rich cyclohexane solvent system and further polymerization can be conducted in pure cyclohexane or a mixed solvent of decreased chloroform content. This process results in the formation of polyamide microcapsules.

A preferred first monomer is 1, 6 hexane diamine, but many other multifunctional, water soluble amines may be used. Microcapsules having a permeability limit below about 1000 daltons have been made using tetraethylene pentamine as the hydrophilic monomer. Terephthaloyl chloride is a preferred complementary monomer, but others, e.g., sebacyl and azelaic acid halides may also be used. It is also within the scope of the invention to use a polyfunctional first or second monomer together with the difunctional monomers so that a certain amount of crosslinking occurs during formation of the membrane. In general, the inclusion of monomers which result in the formation of cross-links has the effect of lowering membrane permeability.

The foregoing reaction system is disclosed merely by way of example. Thus, various aliphatic, alicyclic, and aromatic hydrocarbons may be used for the nonpolar component of the continuous phase, and these may be modified as desired with miscible organic solvents containing various polarity imparting moieties. Petroleum ether fractions, mixed as appropriate with halogenated organic solvents may be used. In general, the only requirements for the solvent system are that:

1. mutually immiscible solvents or solvent systems must be used for the continuous and discontinuous phases;
2. the respective solvents must be of the type which do not interfere with the polymerization reaction between the two or more complementary monomers employed; and
3. in the embodiment of the process where the initially used solvent is mixed with another to alter polarity, there must be available a solvent of a polarity distinctly different from that employed in the continuous phase of the first stage reaction. This solvent must be miscible with the continuous phase, so that its polar character can be significantly varied.

The criteria for selecting a polymer system for use in the process are as follows:

1. one of the two monomers must be hydrophilic and its complementary monomer must be hydrophobic;
2. the two monomers must spontaneously react on contact to form polymer chains insoluble in both phase; and
3. reaction of the selected monomers should be inhibited as little as possible by the presence of the solvents used in the respective phases of the reaction system.

Regarding point 3, it should be noted that some degree of solvent interference, i.e., hydrolysis side reactions, is unavoidable. However, it is an important aspect of the invention that some hydrolysis of the hydrophobic monomer can be tolerated without seriously affecting the quality of the membrane. This is especially true in the embodiment of the invention where the continuous phase is replaced by fresh solvent. In this case, the raw capsules are separated from hydrolysis reaction products when removed from the initial suspension. Also, the local concentration of hydrolyzed monomer can be minimized by adding monomer to the continuous phase in increments.

Polycondensation reactions are well suited in the process of the invention, but polyaddition reactions may also be employed. By astute selection of solvents, chosen in accordance with the teachings herein to suit particular polymer systems and particular materials to be encapsulated, those skilled in the art will be able to produce capsule membranes of, for example, polyester, from a polyol and a diacid halide, other polyamides from diamines and diacid halides, polyurea from diamines and diisocyanates, and polysulfonamide from a difunctional sulfonyl halide and a diamine. Encapsulation procedures using other polyaddition reactions, such as the type disclosed in the Kan et al. U.S. Pat. No. 3,864,275 are also within the scope of this invention.

Capsules produced in accordance with the invention have a variety of uses. For example, they can serve as a chromatographic separation material such as a molecular sieve for separating a mixture of materials on the basis of differences in molecular weight. Advantageously, the capsules are well suited for separating materials of relatively low molecular weight, e.g. on the order of 100 to 5000 daltons. Detoxicants such as activated charcoal may be included within the microcapsules to produce a material capable of absorbing materials from a mixture of solutes passed therethrough. Also, antibodies and other specific binding materials may be encapsulated for use in affinity chromatography. Further particulars on the use of capsules made in accordance with the invention are disclosed in the aforementioned copending applications and in U.S. application S.N. (attorney docket No. 030,848), filed on even date herewith.

The invention will be further understood from the following nonlimiting examples.

EXAMPLE 1

4,4' diamino-biphenyl-2,2' disulfonic acid (DBDSA) (Technical Grade-Eastman Kodak Co.) is prepared by adding approximately 50 grams of DBDSA in 800 ml of deionized water containing 50 ml of 6 M NaOH. The solution is filtered to remove any remaining solids and the DBDSA precipitated by adding 70 ml of 50% v/v HCl. After the crystals have settled, as much of the purple liquid as possible is poured off; then 500 ml 10% v/v HCl is added. The crystals are collected in a Buchner funnel, washed three times which deionized water, washed twice with acetone, and dried. The product is white or pale pink crystals which may be stored in a brown bottle protected from light. This compound is used as an additive to the diamine monomer to form copolymer membranes having a net negative charge to prevent clumping of the microcapsules.

Ten milliliters of a solution containing 30 g/dl hemoglobin are mixed with 10 ml of 3M hexanediamine carbonate solution (pH buffered to approximately 7–9 with $CO_2$) containing 2.88 grams of DBDSA. These two monomers, when mixed, comprised the first reactant in this example. This aqueous solution is then added to 125 ml of prechilled hydrophobic organic liquid made from 100 ml of a 20% chloroform--80% cyclohexane mixture and 25 ml of sorbitan trioleate as an emulsifying agent.

Emulsification is initiated in a prechilled blender and continued for 1 to 2 minutes.

Hot (nearly boiling) cyclohexane is saturated with terephthaloyl chloride (Practical grade - Eastman Kodak Co.) and the solution is quickly filtered. The clear liquid is collected and allowed to cool and crystallize in a closed container. As this compound reacts with atmospheric moisture, the crystals are collected with as little exposure as possible to the atmosphere and dried under a vacuum. A stock solution of terephthaloyl chloride is prepared by dissolving 10.15 grams of purified terephthaloyl chloride in 95 ml of 20% $CHCl_3$—80% $C_6H_{12}$, (v/v.) to produce a 0.5 M solution. This solution should be kept in a tightly sealed container and may be used for at least a month or until precipitate begins to form.

Three ml of the 0.5 M terephthaloyl chloride in 20% chloroform -80% cyclohexane organic solution are then added to the emulsion while blending at a low speed. The actual concentration ratio of diamine/diacid halide is 128 to 1, although some variation is tolerable. At the end of three minutes, the first stage of polymerization is complete, and the suspension is centrifuged for 15 to 20 seconds at 400 to 500 xg. The supernatant organic liquid is then removed by aspiration, and the "raw" capsules washed.

The capsules are then resuspended in a second liquid consisting of 100 ml cyclohexane and 10 ml sorbitan trioleate. While mixing slowly, 7.0 ml of 0.5 M terephthaloyl chloride in 20% chloroform - 80% cyclohexane organic solution are added. This hydrophobic liquid contains only 1.0 to 1.5% chloroform versus 20% in the first organic stage. The reduced chloroform content cuts down the solubility of diamine in the solvent thereby decreasing the affinity of the continuous phase for the diamine, confining further reaction within the framework of the original membrane, and patching macroporous defects. The diamine/diacid halide concentration ratio is 50 to 1. Stirring is continued for 3 minutes, at which time the reaction is quenched by the addition of 30 ml of 50% sorbitan monolaurate buffered to neutral pH with 0.3 M $NaHCO_3$.

In the foregoing procedure the hemoglobin solution is at no time exposed to a pH less than 5 or greater than 9. Hexanediamine solution has a natural pH of 11.5 and a pH of about 11 when mixed with hemoglobin. Bubbling $CO_2$ through the solution causes the production of $H_2CO_3$ and hexanediamine carbonate. The $CO_2$ acts as a buffer and is preferred over sodium salts or weak acids. Before buffering, the sorbitan monolaurate used has a typical pH of approximately 4.5. Extended exposure to this acidic environment denatures the hemoglobin as well as other labile materials sought to be encapsulated. This can be avoided by buffering the sorbitan monolaurate to have a pH close to 7. The purpose of the sorbitan monolaurate is to facilitate transfer of the microcapsules into an aqueous medium such as saline (see Artificial Cells, chapter 2). It should be noted that sorbitan monolaurate tends to react slowly with the terephthaloyl chloride to produce a sticky polymer coating and to crenate the microcapsules. A superior alternative procedure is to remove as much of the solvent as possible by centrifugation and then follow through with the above described procedure.

Microcapsules produced by this process do not allow leakage of hemoglobin (MW=65,000). Half equilibrium times (t ½) for solutes of various molecular weights are given in TABLE I.

TABLE I

| PERMEABILITY OF MICROCAPSULES - HALF EQUILIBRIUM TIMES | | |
|---|---|---|
| Substance | Molecular Weight | t ½ SEM (sec.) |
| Glycerol | 92 | 1.75 ± .1 |
| Diacetone Alcohol | 116 | 2.5 ± .2 |
| Glucose | 180 | 4.9 ± .1 |
| Sucrose | 342 | 10.6 ± .2 |
| Tris[a] | 121 | 2.8 ± .1 |
| Bicine[b] | 163 | 6.1 ± .3 |
| CAPS[c] | 221 | 8.0 ± .5 |
| Pipes[d] | 302 | 13.0 ± .5 |

[a] Tris (hydroxymethyl) aminomethane, pH 8
[b] N,N-bis (2-Hydroxyethyl) glycine, pH 8
[c] Cyclohexylaminopropane sulfonic acid, pH8
[d] Piperazine-N-N'bis (2-ethane sulfonic acid), pH 8

This example demonstrates that the process of the invention is capable of producing selectively permeable microcapsules. Since the hemoglobin can interact with oxygen after encapsulation to a significant degree, this example also demonstrates that the membranes can be formed while preserving the operability of an easily denatured material. These microcapsules behave as a molecular sieve, and may be used to separate solutes in the molecular weight range of about 100–2000 daltons.

EXAMPLE 2

The activity of four enzymes, lactate dehydrogenase (LDH), glutamate oxaloacetate transaminase (GOT), urease, and - glucuronidase was measured before and after encapsulation in the manner set forth above. LDH and GOT were found naturally in the red cell hemolysate. Urease and β-glucuronidase were added in the form of lyophilized, partially purified enzyme, available from commercial sources. The results of the comparisons of activity for LDH, GOT, and urease are set forth in TABLE II. Activity was measured in international units (IU) per liter of sample under conditions of the test reaction. The yields determined for β-glucuronidase were uniformly above 50%.

TABLE II

| Enzyme | Activity (IU/l) SEM | Retained activity (%) |
|---|---|---|
| LDH | 4120 ± 90 | 55 |
| GOT | 1200 ± 80 | 66 |

TABLE II-continued

| Enzyme | Activity (IU/l) SEM | Retained activity (%) |
| --- | --- | --- |
| Urease | 234000 ± 8000 | 68 |

*The enzyme activity of the microcapsules divided by the enzyme activity of the hemolysate used in preparing the microcapsules. (% yield) (SEM = standard error for the mean).

This example illustrates that operable enzymes can be immobilized within the capsules and can react with their respective, lower molecular weight substrates.

EXAMPLE 3

The procedure is the same as that given in Example 1 except that DBDSA is not included in the hemolysate solution. The quantity of the acid chloride used in both polymerization stages, e.g., 0.35 ml acid chloride per ml of hydrophilic solution, is added in equal increments during each polymerization at 30 second intervals instead of all at once at the beginning of polymerization. This procedure keeps the local concentration of the acid chloride low and produces a high quality membrane. Percent enzyme yield is comparable to that described in Example 1.

EXAMPLE 4

Sebacyl chloride-hexanediamine carbonate microcapsules are produced using the procedure of Example 1, except that sebacyl chloride is substituted for terephthaloyl chloride and no DBDSA is used. This procedure produced microcapsules with properties similar to those of microcapsules of Example 1.

EXAMPLE 5

1.5 ml of bovine serum albumin (30%) is added to 1 ml of the hexanediamine carbonate solution of Example 1 together with 0.4 ml 36% KCl and 0.1 ml 2.9 M tetraethylenepentamine (previously adjusted to pH 9.5 with HCl). 4.0 ml of SPAN 85 and 10 ml of the cyclohexane-chloroform solvent of Example 1 is then added to the mix and an emulsion is produced, in 1–2 minutes, by vigorous stirring using a magnetic stirring bar. The terephthaloyl chloride solution (0.4 ml of 0.5 M in cyclohexane-chloroform solvent of Example 1) is added in 0.1 ml increments every 30 seconds, followed by additional 0.1 ml additions every minute for the next 6 minutes.

After centrifuging to separate the capsules, the supernatant is discarded, and the raw microcapsules are resuspended in cyclohexane containing 5% SPAN 85. 0.7 ml terethaloyl chloride are added, and the suspension is stirred for 3 minutes. After separation of the phases by centrifugation, the microcapsules are washed once in pure cyclohexane and subjected to final washing and recovery as indicated in Example 1. The tetraethylenepentamine cross-links the polymer to form strong, uniform permeability membranes useful as a chromatographic material for separating solutes within the 100–1000 dalton range.

EXAMPLE 6

One and one-half milliliter of an aqueous carrier solution comprising polyvinyl pyrrolidone, albumin, and 250 μl of antisera to thyroxine are mixed with 50 μl of 0.5 M tetraethylenepentamine carbonate (pH = 8.2 − 8.6). The aqueous phase is then added to 15 ml of cyclohexane containing 3%–6% ARLACEL (sorbitan oleate) as an emulsifier. The two-phase system is emulsified by means of a magnetic stirring bar, and as stirring continues, one 2 ml portion of 4:1 (v/v) cyclohexane-chloroform solution containing 0.1 mg/ml terephthaloyl chloride is added to initiate polymerization.

Sixty seconds later, another 0.8 ml of the terephthaloyl chloride solution is added. After 60 more seconds, 0.5 ml of pure chloroform are added to increase the affinity of the continuous phase for the polyfunctional amines; then, at 30 second intervals, three additional 0.5 ml increments of pure chloroform are added.

After a total reaction time of four minutes, the emulsion is gently centrifuged and the supernatant liquid discarded. The microcapsules are washed with pure cyclohexane and a 50% aqueous TWEEN-20 solution (sorbitan monolaurate) buffered to neutral pH with 0.3 M $NaHCO_3$.

The foregoing procedure results in capsules having a permeability sufficient to allow passage of thyroxin, (molecular weight 777 daltons) and lower molecular weight materials, yet insufficient to allow leakage of antibody from the interior of the capsules.

EXAMPLE 7

Two and one-half ml of an aqueous carrier solution comprising polyvinyl pyrrolidone, albumin, $Na_2CO_3$/$NaHCO_3$ buffer, and 0.3 ml of glucose oxidase are mixed with 1.2 ml of hexanediamine carbonate (2.5 M; pH 8.4–8.6). This aqueous phase is then added to 30 ml of a mixed organic solvent consisting of 50 parts cyclohexane, 5 parts chloroform, and 3%–5% sorbitan oleate as an emulsifier. The two-phase system is emulsified by means of an emulsifying stirring probe.

While stirring, 2.6 ml of the terephthaloyl chloride solution of Example 6 is added to initiate polymerization. Another 0.8 ml aliquot of the terephthaloyl chloride solution is added 30 seconds later. This is followed by the addition of four 5.0 ml volumes of cyclohexane, spaced at 30 second intervals.

At the end of 3.5 minutes of total polymerization reaction time, the reaction is terminated and the microcapsules harvested as set forth in Example 6. Glucose oxidase is retained within the capsules, yet glucose (MW≃180) diffused through the membranes.

EXAMPLE 8

A 4.0 ml aqueous phase comprising 1.25 M hexanediamine carbonate and lactate dehydrogenase are emulsified in 20 ml of pure cyclohexane containing 2% non-ionic surfactant (Arlecel). While stirring vigorously, membrane formation is initiated as toluene diisocyanate is added to the emulsion. A total of 75 μl of the diisocyanate is added by means of an infusion pump over a period of 8½ minutes as a 5.0 ml aliquot of solution consisting of 90% cyclohexane - 10% chloroform. The affinity of the continuous phase for the diamine is thus continually increased until all of the cyclohexane-soluble diisocyanate has been added. The system is then stirred for an additional 20 minutes. Two minutes before isolating the capsules, the tackiness of the surface of the membranes is reduced by adding 0.6 ml 10% terepthaloyl chloride. These capsules are permeable to substances in the molecular weight range below about 1000 daltons.

EXAMPLE 9

Hexanediamine carbonate (pH = 8.5 ± 0.1) solution is prepared by mixing 17.7 ml 1,6 hexanediamine with 32 ml of water, and bubbling $CO_2$ through the solution for about 1 hour or until the pH level is reached. Terephthaloyl chloride (TCl) solution is prepared by adding 20 g TCl in 200 ml of organic solvent consisting of 4 parts cyclohexane and 1 part chloroform. TCl is dissolved by stirring vigorously, and the solution is then centrifuged for 10 minutes at 2600 rpm. Any precipitate is discarded.

750 ml cyclohexane are mixed with 125 ml SPAN-85 in a 2-liter mixer equipped with a magnetic stirring bar. While stirring, a mixed solution made from 25 ml of 15% polyvinyl-pyrrolidone - 4% bovine serum albumin, 40 ml of phosphate buffered saline premixed with 5 ml of antiserum, and 30 ml of hexanediamine carbonate solution is added to the cyclohexane. When droplets of the desired size have been produced, 70 ml TCl solution are added. Thirty seconds later, 37.5 ml of TCl are added. Sixty seconds later, 25 ml of chloroform are added, and three additional 25 ml aliquots of chloroform are added at 30 second intervals.

The microcapsules are recovered by centrifuging the two-phase reaction system, decanting the supernatant, and mixing the capsules with TWEEN-20 (buffered with $NaHCO_3$) and phosphate buffered saline. The capsules contain polyvinylpyrrolidone and bovine serum albumin as filler materials. Substances having a molecular weight in excess of about 20,000 daltons (such as most antibodies) cannot penetrate the membranes. Substances having a molecular weight below about 5000 daltons penetrate the membranes.

Other embodiments are within the following claims.

We claim:

1. A process for producing microcapsules comprising membranes having an upper limit of permeability within a selected range, said process comprising the steps of:
   A. forming a two-phase system comprising
      a hydrophobic continuous phase and
      a discontinuous phase of discrete aqueous droplets containing a first hydrophilic monomer selected from the group consisting of multifunctional alcohols and amines, said first monomer being capable of forming a polymer by reaction with a second, complementary hydrophobic monomer selected from the group consisting of diacid halides, diisocyanates, and difunctional sulfonyl halides;
   B. dissolving a portion of said second monomer in the continuous phase to effect interfacial polymerization about the droplets of the discontinuous phase;
   C. altering the affinity of the continuous phase for said first monomer by changing the polarity of the continuous phase during the polymerization of said first and said second monomers;
   D. allowing said first and second monomers to further polymerize at the interface of the altered continuous phase; and
   E. terminating the interfacial polymerization when microcapsules of the selected permeability have been produced.

2. The process of claim 1 wherein, in the two-phase system of step A, the continuous phase has a low affinity for said first monomer so that a thin membrane is produced in step B, and in step C, the affinity of the continuous phase for the first monomer is increased and an additional layer of polymer is produced about the droplets of the discontinuous phase.

3. The process of claim 2 wherein the affinity of the continuous phase for the first monomer is increased by replacing the continuous phase with a solvent more polar than the solvent used in the continuous phase formed in step A.

4. The process of claim 2 wherein the affinity of the continuous phase for the first monomer is increased by diluting the continuous phase with a polar solvent.

5. The process of claim 4 wherein the polar solvent is added in increments over the course of the polymerization reaction.

6. The process of claim 1 wherein, in the two-phase system of step A, the continuous phase is selected to have a relatively high affinity of the first monomer so that membranes comprising a thick polymer network are produced in step B, and in step C, the affinity of the continuous phase for the first monomer is decreased so that further polymerization occurs preferentially within the polymer network.

7. The process of claim 1 wherein a substance incapable of traversing the membranes produced in step D is included in the aqueous droplets of step A as a filler material.

8. The process of claim 7 wherein the filler material is selected from the group consisting of polyvinyl pyrrolidone, polyethylene glycol, polysaccharides, and albumin.

9. The process of claim 1 wherein the first monomer is selected from the group consisting of 1,6 hexanediamine, tetraethylenepentamine, and mixtures thereof.

10. The process of claim 9 wherein said second monomer is selected from the group consisting of terephthaloyl chloride, sebacyl chloride, and mixtures thereof.

11. The process of claim 1 wherein the first monomer is a multifunctional amine and the second monomer is a diacid halide.

12. The process of claim 1 wherein second monomer is added in increments during the course of the polymerization reaction.

* * * * *

UNITED STATES PATENT AND TRADEMARK OFFICE
CERTIFICATE OF CORRECTION

PATENT NO. : 4,251,387
DATED : February 17, 1981
INVENTOR(S) : Franklin Lim et al It is certified that error appears in the above-identified patent and that said Letters Patent are hereby corrected as shown below:

Column 1, line 46, "wihin" should read --within--.

Column 1, line 54, "ay" should read --any--.

Column 2, line 42, insert --the-- after "for."

Column 6, line 61, delete "(attorney docket No. 030,848)" and substitute therefor --030,848--.

Column 7, line 8, "which" should read --with--.

Signed and Sealed this

Twelfth Day of May 1981

[SEAL]

Attest:

RENE D. TEGTMEYER

Attesting Officer  Acting Commissioner of Patents and Trademarks